United States Patent
Shields et al.

(10) Patent No.: US 9,561,320 B2
(45) Date of Patent: Feb. 7, 2017

(54) DEVICE FOR PROMOTING FISTULA PATENCY AND METHOD

(71) Applicant: Cook Medical Technologies LLC, Bloomington, IN (US)

(72) Inventors: Adam Shields, Lafayette, IN (US); Keith Milner, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 36 days.

(21) Appl. No.: 14/667,999

(22) Filed: Mar. 25, 2015

(65) Prior Publication Data

US 2015/0352272 A1 Dec. 10, 2015

Related U.S. Application Data

(60) Provisional application No. 62/008,199, filed on Jun. 5, 2014.

(51) Int. Cl.
*A61M 5/00* (2006.01)
*A61M 1/36* (2006.01)
*A61B 17/11* (2006.01)
*A61F 2/06* (2013.01)

(52) U.S. Cl.
CPC .............. *A61M 1/3655* (2013.01); *A61B 17/11* (2013.01); *A61B 2017/1107* (2013.01); *A61B 2017/1135* (2013.01); *A61F 2002/068* (2013.01); *A61M 2205/3331* (2013.01)

(58) Field of Classification Search
CPC . A61B 17/11; A61B 17/064; A61B 17/12009; A61B 2017/1107; A61B 2017/1135; A61M 27/002; A61M 39/10; A61M 1/3655; A61F 2/06

USPC .............................................. 604/6.16, 8–10
See application file for complete search history.

(56) References Cited

U.S. PATENT DOCUMENTS

| | | | |
|---|---|---|---|
| 5,344,425 A | 9/1994 | Sawyer | |
| 6,616,675 B1 | 9/2003 | Evard et al. | |
| 7,128,750 B1 | 10/2006 | Stergiopulos | |
| 7,331,989 B2 | 2/2008 | Houston et al. | |
| 7,682,673 B2 * | 3/2010 | Houston | A61F 2/06 428/35.8 |
| 8,382,697 B2 | 2/2013 | Brenneman et al. | |
| 8,523,800 B2 | 9/2013 | Brenneman et al. | |
| 2009/0036817 A1 * | 2/2009 | Dakin | A61B 17/11 604/8 |
| 2013/0110029 A1 | 5/2013 | Dakin et al. | |
| 2013/0331928 A1 | 12/2013 | Yang et al. | |

FOREIGN PATENT DOCUMENTS

| | | |
|---|---|---|
| EP | 2136734 | 10/2008 |
| WO | 9844869 | 10/1998 |
| WO | 0038591 | 7/2000 |
| WO | 2010133848 | 11/2010 |

* cited by examiner

*Primary Examiner* — Philip R Wiest
(74) *Attorney, Agent, or Firm* — Liell & McNeil

(57) ABSTRACT

A device for promoting patency of a fistula includes an annular body and a plurality of vanes formed integrally with the annular body, and projecting inwardly from an inner radial surface thereof. The vanes are oriented so as to impart circumferential velocity components to blood passed through a lumen of the device, and such that an unobstructed line of sight parallel to a central axis of the annular body extends between adjacent ones of the vanes.

16 Claims, 3 Drawing Sheets

DEVICE FOR PROMOTING FISTULA PATENCY AND METHOD

TECHNICAL FIELD

The present disclosure relates generally to devices used in fistula formation, and more particularly to a device for promoting fistula patency by way of inducing circumferential velocity components in blood flow.

BACKGROUND

Renal disease is a significant health challenge in the United States and elsewhere. Lack of organ transplant availability means that most patients are treated by dialysis, with roughly ten times as many patients receiving hemodialysis versus other forms. To minimize treatment time, hemodialysis requires a relatively large blood volume flow rate typically achieved through an arteriovenous shunt created through surgery. This shunt creates a low resistance pathway that can result in significantly increased flow rate through an arteriovenous fistula. Grafts have also been widely used.

In recent years, arteriovenous fistulas have been increasingly used to the exclusion of grafts, as data has emerged demonstrating that fistulas tend to have better long term patency rates and reduced requirements for intervention. There are nevertheless various challenges associated with fistula usage. After surgical creation of an arteriovenous fistula, the inflow and outflow vessels must dilate sufficiently and the venous tissue must generally undergo a remodeling process known as fistula maturation in order to be able to sustain the high flow rates needed for dialysis. This maturation process is only successful in about sixty percent of arteriovenous fistulas.

Another common problem is tissue proliferation along the lumen of the vein know as neointimal hyperplasia or NIH. NIH may lead to stenosis, reduced flow and ultimately failure of the fistula. Abnormal flow through an arteriovenous fistula is often observed with auscultation in the nature of characteristic vibration, believed likely to stem from turbulent flow through the vasculature. Various devices and techniques for use in fistula formation have been proposed over the years. Such technologies, however, suffer from a variety of drawbacks and shortcomings as evidenced by the still relatively low success rates of fistula maturation. Moreover, some devices for fistula formation are purpose-engineered for certain specific applications and may be less well suited to others. U.S. Pat. No. 8,523,800 to Brenneman et al., contemplating a shunt rivet for implantation in the aorta and inferior vena cava, is one such example.

SUMMARY

In one aspect, a device for promoting patency of an arteriovenous fistula includes an annular body defining a center axis and have a first axial end, a second axial end, an outer radial surface, and an inner radial surface defining a central lumen extending from the first axial end to the second axial end. The device further includes a plurality of flow-directing vanes formed integrally with the annular body in projecting inwardly from the inner radial surface. Each of the vanes has an inner edge, an outer edge, a leading edge, and a trailing edge. Each of the leading edges are spaced axially outward of the first axial end, and each of the trailing edges are spaced axially outward of the second axial end. Each of the plurality of vanes further has a circumferentially and axially advancing orientation such that an unobstructed line of sight parallel to the center axis extends between adjacent ones of the plurality of vanes.

In another aspect, a method of connecting blood vessels in a patient includes forming an arteriovenous fistula so as to create a fluid flow path that fluidly connects a first vessel and a second vessel in the patient, and implanting a medical device within the patient such that a lumen of the device is within the fluid flow path. The method further includes establishing blood flow communication between the first and second vessels such that blood conveyed through the fluid flow path impinges upon a vane within the lumen, and inducing circumferential velocity components in the blood via the impingement so as to promote patency of the fistula.

DETAILED DESCRIPTION

Figure 1:
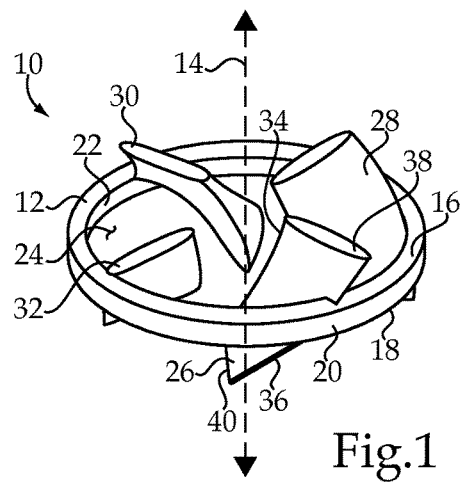
FIG. 1 is a perspective view of a medical device, according to one embodiment.

Referring to FIG. 1, there is shown a medical device 10 for promoting patency of an arteriovenous fistula in a patient. Device 10 includes an annular body 12 defining a center axis 14, and having a first axial end 16 and a second axial end 18. Annular body 12 further includes an outer radial surface 20, and an inner radial surface 22 defining a central lumen 24 extending from first axial end 16 to second axial end 18. Device 10 further includes a plurality of flow-directing vanes 26, 28, 30 and 32 formed integrally with annular body 12 and projecting inwardly from inner radial surface 22. The present description of features of a single one of vanes 26, 28, 30 and 32 should be understood to refer hereinafter analogously to any of the vanes. Vane 26 has an inner edge 34, an outer edge 36, a leading edge 38, and a trailing edge 40. Device 10 may have various forms of symmetry, including end-to-end symmetry such that device 10 has a substantially identical appearance when viewed end on from either axial direction. Each leading edge 38 is spaced axially outward of first axial end 16, whereas each trailing edge 40 is spaced axially outward of second axial end 18.

Figure 2:
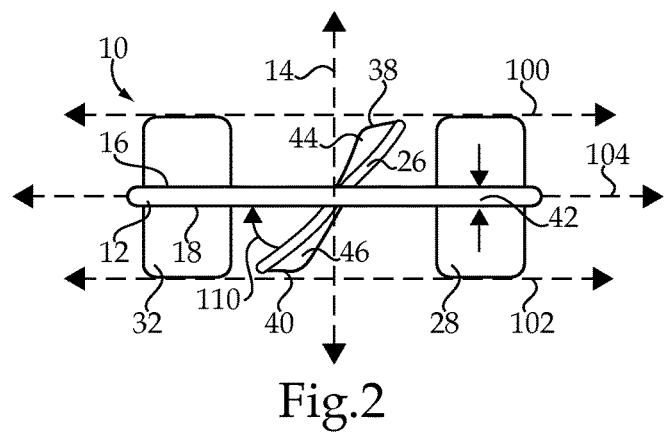
FIG. 2 is a side view of the medical device of FIG. 1.
Figure 3:
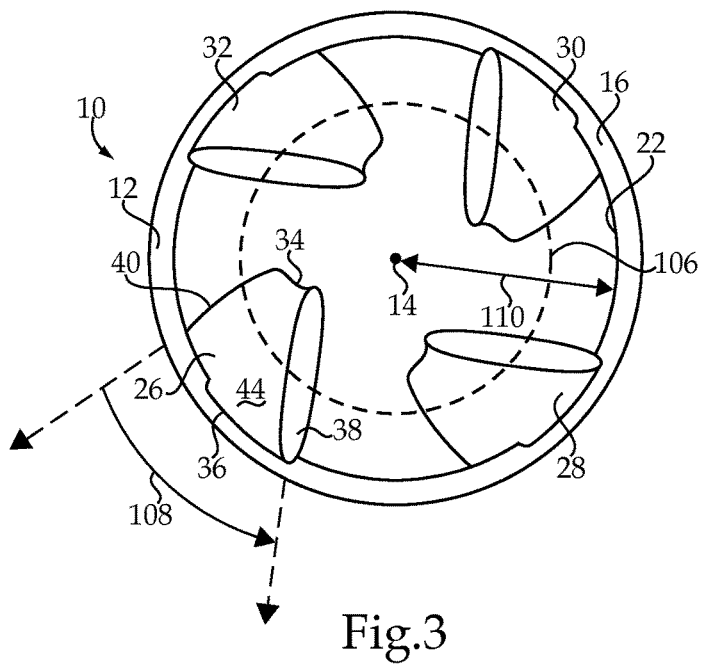
FIG. 3 is a top view of the medical device of FIGS. 1 and 2.

Each of vanes 26, 28, 30 and 32 has a circumferentially and axially advancing orientation such that an unobstructed line of sight parallel to center axis 14 extends between adjacent ones of vanes 26, 28, 30 and 32. In FIG. 1 it can be seen that vane 26 is adjacent to vane 32. An unobstructed line of sight parallel axis 14 extends between vanes 26 and 32. Referring also to FIG. 2 and FIG. 3, the unobstructed line of sight is readily apparent between any two adjacent vanes 26, 28, 30 and 32. It will be appreciated that device 10 can be tilted so as to be viewed from various different angles, where a line of sight between adjacent ones of the vanes is obstructed. For instance, in FIG. 1, no line of sight between vane 26 and vane 28 is apparent due to the angle of observation. In FIG. 3, it can be seen that there is no overlap in an axial projection between any of the vanes at all, the significance of which will be apparent from the following description.

Also illustrated in FIG. 2 is a tangent line indicating a tangent plane 100 viewed edge-on, and defined by coplanar and axially outermost points of leading edge 38 and the leading edges on the other vanes. Tangent plane 100 is oriented normal to center axis 14. A second tangent line and tangent plane 102 is analogously defined by trailing edge 40 and the other trailing edges, and also oriented normal to center axis 14. In a practical implementation strategy, first and second tangent planes 100 and 102 are equidistant from an axial section plane 104 bisecting annular body 12. It can also be seen from the drawings, and in particular FIG. 2, that each vane is non-uniform in pitch, and has a twisted shape such that the corresponding leading and trailing edges 38 and 40 are not parallel in an axial projection. Each vane further may be understood to include an upstream surface 44, and a downstream surface 46. In versions where device 10 is symmetric about a bisecting axial section plane, the choice of which surface is labeled an upstream surface and which is labeled a downstream surface can be arbitrary. In a non-symmetrical design, device 10 could be specially adapted upon implantation in a patient to have one end oriented toward incoming blood flow, while the other end is oriented away from incoming blood flow. Such special adaptations could include orienting leading vane edges at a relatively shallow angle to incoming blood flow, and orienting trailing vane edges at a steeper angle to incoming blood flow, with an orientation of the vanes steepening from the leading to the trailing edges. It will be readily visualized that a relative extent of axial advancement of vanes in such a design could be understood to decrease as one moves downstream.

Each leading edge 38 and each trailing edge 40 may further have a rounded contour, roughly peaking at a center point of the corresponding leading or trailing edge, so as to define a circle at points of intersection with the corresponding tangent plane. In FIG. 3, circle 106 is shown, defined in this manner. Circle 106 is centered on center axis 14, and in a practical implementation strategy positioned from about one-third to about two-thirds of a radial distance 110 between center axis 14 and inner radial surface 22. Also in a practical implementation strategy, inner edge 34 is positioned closer to center axis 14 than to inner radial surface 22. A radially inward extent of vanes according to the present disclosure may be substantially uniform throughout, although in alternative embodiments the radially inward extent might vary from a location of the leading edge to a location of the trailing edge, being greatest near an axial midpoint of the device, for instance. In the illustrated embodiment, a number of the vanes is 4. Other embodiments are contemplated herein where a number of the vanes is 3 or 5, and potentially could be 2 or 6 in other embodiments, or possibly an even greater number.

With continued reference to FIGS. 1, 2 and 3, annular body 12 may have an axial thickness 42 from first axial end 16 to second axial end 18. It can be seen that an axial extent of the vanes is several times greater than axial thickness 42 upon each side of annular body 12. In other words, the vanes may project axially outward of the corresponding axial end of body 12 a distance which is several times greater than an axial thickness of annular body 12 between axial ends 16 and 18. In a practical implementation strategy, the axial spacing of the vanes in either direction from annular body 12 may be about four times axial thickness 42, and in other embodiments could be from two times to six times, or perhaps even greater.

It will be appreciated that axial thickness 42 generally determines an axial length of lumen 24. It will generally be desirable to impart sufficient circumferential velocity components to blood passed through lumen 24 to obtain desirable improvements or promotion of fistula patency without inordinately occluding the available flow area for blood. The present disclosure can be understood as teaching a design with geometry and relative feature sizes optimized so as to balance a desire to relatively aggressively impart circumferential velocity components, or helical flow, with the desire to avoid inordinately occluding the flow area. Such factors include axial thickness 42, axial extent of vanes 26, 28, 30 and 32, and their twisted shape as well as angle of inclination relative to annular body 12. While the vanes may be uniform or non-uniform in pitch, in one practical implementation strategy an angle 110 is defined by vane 26 and axial end 18 at outer edge 36 which is from about 30° to about 60°. An analogously defined angle at inner edge 34 might be a few degrees, for instance about 5-10°, greater given the twisted shape of vane 26 that orients leading edge 38 and trailing edge 40 at an angle to one another. To this end, an angle 108 may be defining by leading edge 38 and trailing edge 40, and might also be from about 30° to about 60°, although the present disclosure is not thereby limited. It can also be seen from FIG. 3 in particular that leading edge 38 and trailing edge 40 are not oriented along a radius line from center axis 14 to inner radial edge 22. Another way to understand this feature is leading edge 38 and trailing edge 40 are not oriented normal to a line tangent to inner radial edge 22. In the illustrated embodiment, leading edge 38 and trailing edge 40 may be oriented so as to define an included angle less than 30° with a radial line extending from axis 14 to inner radial surface 22, in an axial projection.

INDUSTRIAL APPLICABILITY

Figure 4:
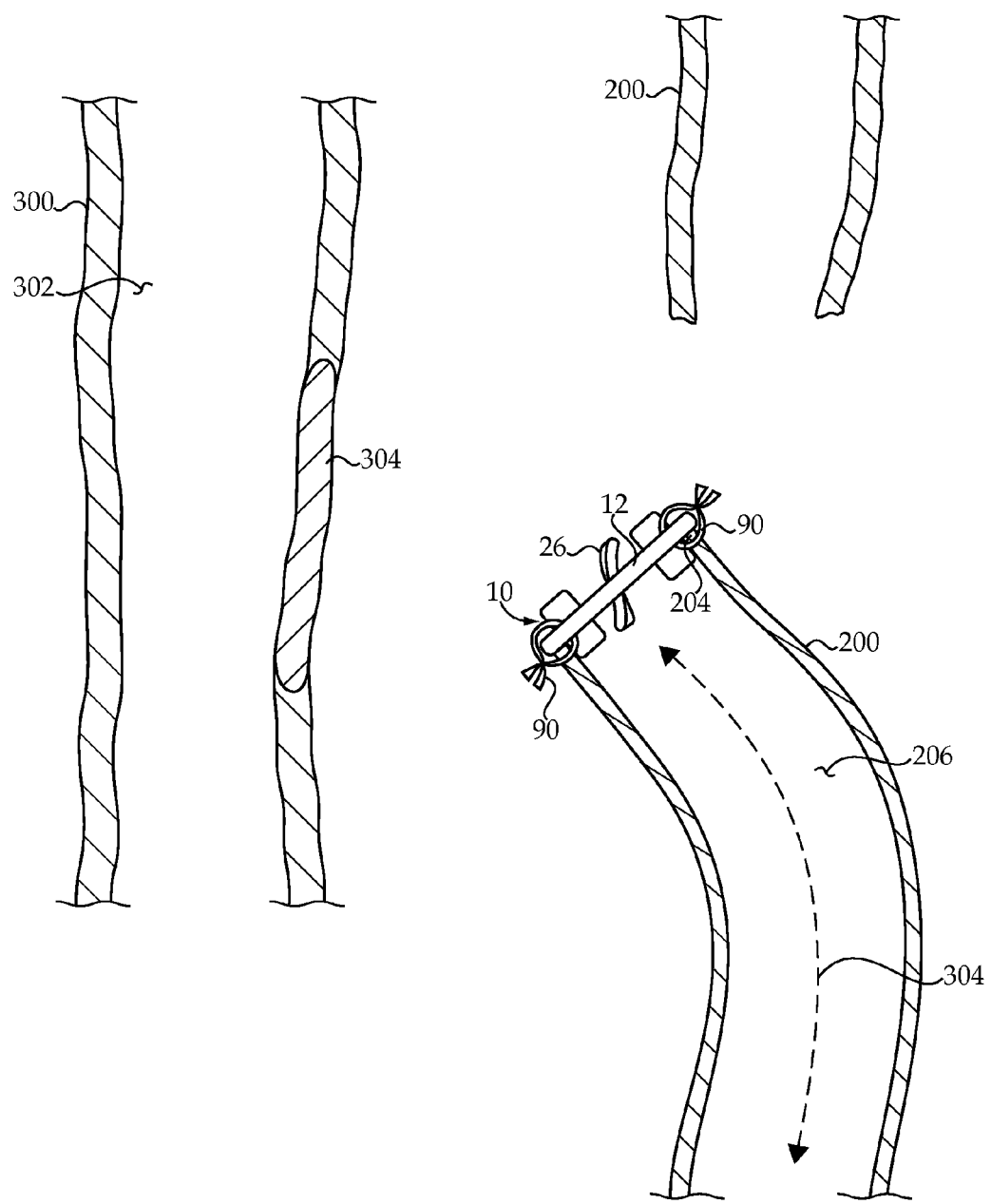
FIG. 4 is a diagrammatic view at one stage of a procedure, according to one embodiment.

Referring to the drawings generally, but in particular now to FIG. 4, there is shown a first vessel 200 having been severed, such as by a physician with a surgical cutting tool, to render an open end 204. Device 10 has been fitted into open end 204, in a manner where lumen 22 is in fluid communication with a vessel lumen 202, and device 10 is generally co-axially aligned with vessel 200. A vessel lumen axis 206 is defined by vessel 200. FIG. 4 also illustrates a second vessel 300 having a vessel lumen 302. An opening in the form of a slit 304 has been formed in the side of vessel 300, such as by a physician with a surgical cutting tool. In a practical implementation strategy, vessel 300 may be an artery, and vessel 200 may be a vein which is to be attached to artery 300 via an arteriovenous fistula so as to create a fluid flow path that fluidly connects vessel 200 and vessel 300 in a patient.

Device 10 is implanted within the patient, and in particular within vessel 200 such that upon forming the arteriovenous fistula lumen 22 will be within the fluid flow path between vessels 300 and 200. In the illustrated embodiment, device 10 has been advanced into vessel lumen 202, such that its vanes project slightly into lumen 202 whereas annular body 12 is snugly positioned up against the cut end of vessel 200. In other embodiments, device 10 could be slipped further into vessel 200, potentially such that the vanes are wholly within vessel lumen 202. Sutures 90 have been used to secure device 10 to vessel 200, and ultimately will serve to secure device 10 within the fistula once formed. It can be seen that sutures 90 are looped through device 10, in particular about annular body 12, in the illustrated embodiment. In other instance, holes might be provided through annular body 12 for receiving sutures, and in still other designs suture loops or other mechanical contrivances such as a hook or even a pierce-able thin membrane might be provided upon device 10 for accommodating sutures, or some other retention mechanism.

Figure 5:
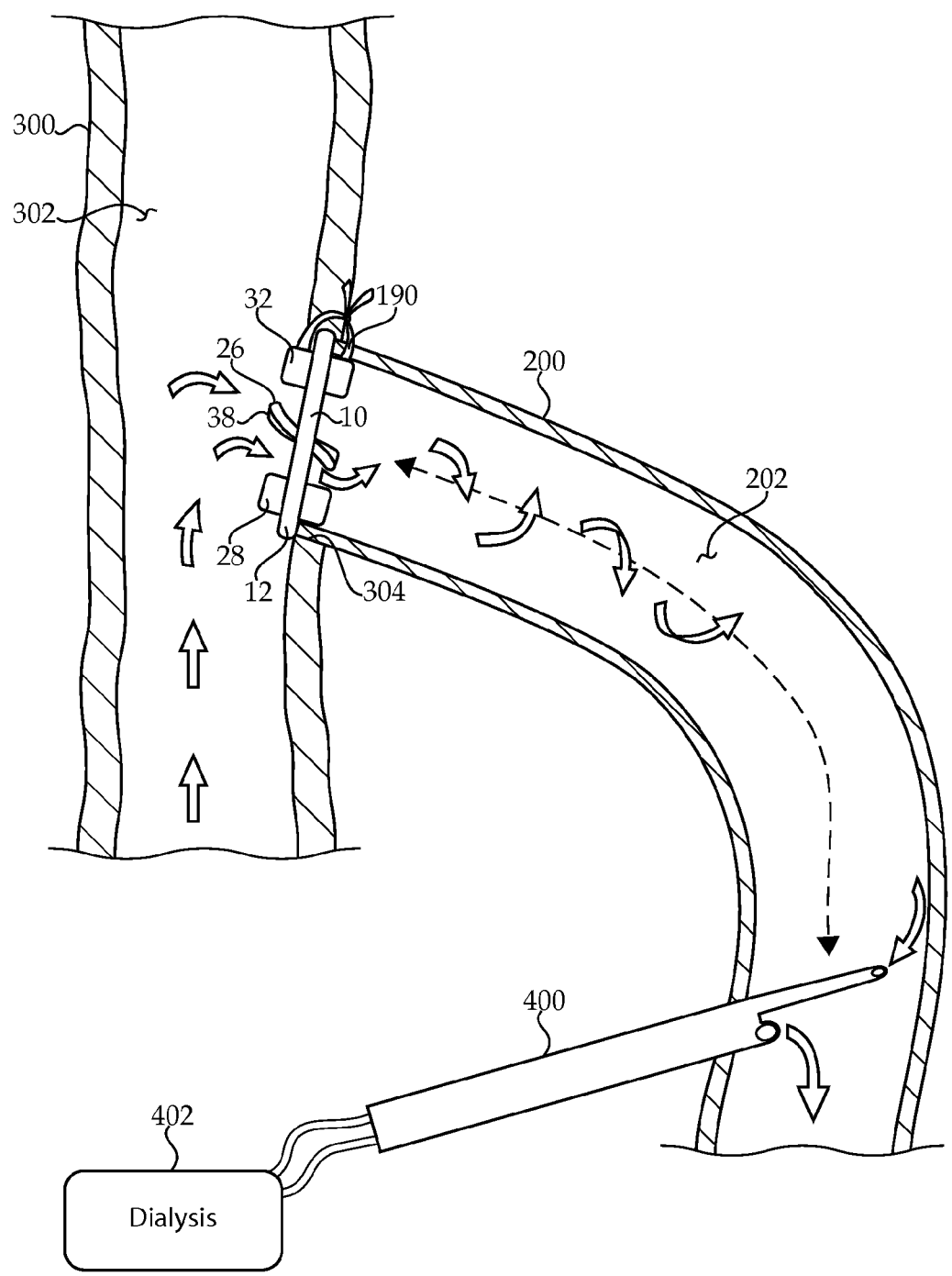
FIG. 5 is a diagrammatic view at one stage of a procedure, according to one embodiment.

Referring also now to FIG. 5, there is shown vessel 200 and vessel 300 where the fistula has been formed, and the vanes project into vessel lumen 202, and also into vessel lumen 302. Additional sutures 190, one of which is shown, may be used to attach vessel 200 to vessel 300, and could also loop about or through annular body 12 or another part of device 10. Formation of the fistula can be used in establishing blood flow communication between vessel 300 and vessel 200 such that blood conveyed through the fluid flow path created by the fistula impinges upon one or more vanes 26 of device 10. The impingement upon the one or more vanes 26 induces circumferential velocity components in the blood conveyed through the fluid flow path so as to promote patency of the fistula. Arrows in FIG. 5 illustrate example patterns of blood flow through the fistula, and it can be noted that blood initially impinging upon leading edges 38 of the one or more vanes 26 is generally directed through device 10, passing through lumen 22, and upon passing fully through device 10 and entering vessel lumen 202 retains some circumferential velocity components generally of a helical nature.

It can also be seen from FIG. 5 that the helical flow continues downstream of device 10, for at least several device lengths. It has been discovered that helical outflow may persist past device 10, potentially for several centimeters. This capability of device 10 and other devices contemplated herein is considered to provide advantages over known fistula formation devices that do not induce such flow, and therefore promotes long term fistula patency. Neointimal hyperplasia or NIH as described above may also be less likely. Related advantages of the present disclosure arise from the simplicity of the design of device 10. In a practical implementation strategy device 10 includes one piece of molded biocompatible polymeric material such as a nylon material or any other suitable material. As suggested above, while implantation just at the intersection of a vane and an artery within a fistula is one practical implementation strategy, the present disclosure is not thereby limited. In other instances it is expected that device 10 could be implanted downstream of a fistula formed by another device, or formed without any fistula formation device at all. It will be recalled that a practical application of fistula formation is in facilitating hemodialysis. In FIG. 5, a dialysis mechanism 402 is shown coupled with a catheter mechanism 400 positioned within vessel 200 to both receive and return blood for conventional dialysis treatment. Mechanism 402 is shown as a combined or double needle dialysis mechanism, although in other instances separate inflow and outflow needles or the like will be used. Rather than a fistula formed for hemodialysis purposes, those skilled in the art will appreciate that the present disclosure may have broader applications.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A device for promoting patency of an arteriovenous fistula comprising:
   an annular body defining a center axis and having a first axial end, a second axial end, an outer radial surface, and an inner radial surface defining a central lumen extending from the first axial end to the second axial end;
   a plurality of flow-directing vanes formed integrally with the annular body and projecting inwardly from the inner radial surface, and each having an inner edge, an outer edge, a leading edge, and a trailing edge, where each of the leading edges are spaced axially outward of the first axial end and each of the trailing edges are spaced axially outward of the second axial end; and
   each of the plurality of vanes further having a circumferentially and axially advancing orientation such that an unobstructed line of sight parallel to the center axis extends between adjacent ones of the plurality of vanes.

2. The device of claim 1 wherein the annular body has an axial thickness extending from the first axial end to the second axial end, and wherein the spacing of the leading and trailing edges axially outward of the first and second axial ends, respectively, is equal to or greater than the axial thickness.

3. The device of claim 1 wherein each of the plurality of vanes is non-uniform in pitch and has a twisted shape.

4. The device of claim 1 wherein the leading edges define a first tangent plane oriented normal to the center axis, and the trailing edges define a second tangent plane oriented normal to the center axis.

5. The device of claim 4 wherein the first and second tangent planes are equidistant from an axial section plane bisecting the annular body.

6. The device of claim 4 wherein each of the leading edges and each of the trailing edges has a rounded contour so as to define a circle at points of intersection with the corresponding tangent plane.

7. The device of claim 6 wherein the circle is centered on the center axis, and positioned from one-third to two-thirds of a radial distance between the center axis and the inner radial surface, and the inner edge of each of the vanes is positioned at a location closer to the center axis than to the inner radial surface of the annular body, and wherein a number of the vanes is from 3 to 5.

8. A method of connecting blood vessels in a patient comprising the steps of:
   forming an arteriovenous fistula so as to create a fluid flow path that fluidly connects a first vessel and a second vessel in the patient;
   implanting a medical device within the patient such that a lumen of the device is within the fluid flow path;
   establishing blood flow communication between the first and second vessels such that blood conveyed through the fluid flow path impinges upon a vane within the lumen;
   inducing circumferential velocity components in the blood via the impingement so as to promote patency of the fistula;
   wherein the step of implanting includes implanting the medical device within the fistula;
   securing the medical device within the fistula via suturing; and
   wherein the annular body defines a center axis, and the vanes project axially outward from opposite ends of the lumen, such that the vanes are exposed within a blood vessel lumen of the patient.

9. The method of claim 8 wherein the medical device includes an annular body defining the lumen, and a plurality of vanes attached to the annular body, and wherein the step of suturing further includes looping a suture through the medical device.

10. The method of claim 8 wherein the step of implanting further includes implanting the medical device such that leading edges of the plurality of vanes are exposed within a lumen of an artery and trailing edges of the plurality of vanes are exposed within a lumen of a vein connected to the artery via the fistula.

11. A device for promoting patency of an arteriovenous fistula comprising:
   an annular body defining a center axis and having a first axial end that defines a first plane, a second axial end that defines a second plane, an outer radial surface, and an inner radial surface defining a central lumen extending from the first axial end to the second axial end; and
   a plurality of flow-directing vanes formed integrally with the annular body and projecting inwardly from the inner radial surface, and at least a portion of at least one of the vanes being outside of a space between the first plane and the second plane.

12. The device of claim 11 wherein a leading edge of each of the plurality of vanes is outside of the space between the first plane and the second plane.

13. The device of claim 11 wherein a trailing edge of each of the plurality of vanes is outside of the space between the first plane and the second plane.

14. The device of claim 13 wherein a leading edge of each of the plurality of vanes is outside of the space between the first plane and the second plane.

15. The device of claim 14 wherein a distance of the leading and trailing edges axially outside the space, respectively, is equal to or greater than an axial thickness between the first plane and the second plane.

16. The device of claim 15 wherein each of the plurality of vanes has a twisted shape.

* * * * *